(12) United States Patent
Li et al.

(10) Patent No.: US 12,265,032 B2
(45) Date of Patent: Apr. 1, 2025

(54) METHOD FOR DETERMINING CIPROFLOXACIN IN MEAT PRODUCT BASED ON ENZYME-LINKED UPCONVERSION FLUORESCENCE AND POTASSIUM TITANIUM OXALATE SYSTEM

(71) Applicant: JIANGSU UNIVERSITY, Zhenjiang (CN)

(72) Inventors: Huanhuan Li, Zhenjiang (CN); Qiyi Bei, Zhenjiang (CN); Zhixiong Qi, Zhenjiang (CN); Quansheng Chen, Zhenjiang (CN); Yiyong Yan, Zhenjiang (CN); Hongzhen Ma, Zhenjiang (CN); Xin Zhang, Zhenjiang (CN); Qin Ouyang, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 18/762,916

(22) Filed: Jul. 3, 2024

(65) Prior Publication Data
US 2024/0353329 A1 Oct. 24, 2024

Related U.S. Application Data

(63) Continuation of application No. PCT/CN2024/081570, filed on Mar. 14, 2024.

(30) Foreign Application Priority Data

Jun. 26, 2023 (CN) .......................... 202310758306.2

(51) Int. Cl.
| | |
|---|---|
| *C12Q 1/18* | (2006.01) |
| *C12Q 1/00* | (2006.01) |
| *C12Q 1/04* | (2006.01) |
| *C12Q 1/689* | (2018.01) |
| *G01N 1/38* | (2006.01) |

(Continued)

(52) U.S. Cl.
CPC .......... *G01N 21/6428* (2013.01); *G01N 1/38* (2013.01); *G01N 33/12* (2013.01)

(58) Field of Classification Search
None
See application file for complete search history.

(56) References Cited

U.S. PATENT DOCUMENTS

| | | |
|---|---|---|
| 2018/0217062 A1 | 8/2018 | Kim et al. |
| 2018/0292317 A1 | 10/2018 | Kim et al. |

FOREIGN PATENT DOCUMENTS

| | | |
|---|---|---|
| CN | 103343116 A | 10/2013 |
| CN | 107402198 A | 11/2017 |

(Continued)

OTHER PUBLICATIONS

Huanhuan Li et al., "A novel enzymatic biosensor for CIP in food based on UCNPs and colorimetric strategy of potassium titanium oxalate", Journal of Food Composition and Analysis, vol. 125, Nov. 11, 2023, 105827, pp. 1-10.

(Continued)

*Primary Examiner* — Neil N Turk (57) ABSTRACT

A method for determining ciprofloxacin in a meat product based on an enzyme-linked upconversion fluorescence and potassium titanium oxalate system is provided. An enzyme-linked upconversion nanoparticle solution is mixed with an aptamer-bound magnetized polydopamine solution to obtain a fluorescence-ultraviolet dual-signal detection system. A fluorescence standard curve and a colorimetric standard curve for the ciprofloxacin content determination are created through the fluorescence-ultraviolet dual-signal detection system in combination with potassium titanium oxalate and hydrogen peroxide. A fluorescence intensity signal characteristic value and an ultraviolet absorbance signal characteristic value of a meat sample solution are determined. A (Continued)

ciprofloxacin content in the meat sample is calculated according to the fluorescence standard curve and the colorimetric standard curve.

6 Claims, 5 Drawing Sheets

Specification includes a Sequence Listing.

(51) Int. Cl.
  *G01N 21/64* (2006.01)
  *G01N 33/12* (2006.01)

(56) References Cited

FOREIGN PATENT DOCUMENTS

| CN | 113176243 | A | 7/2021 | |
|----|-----------|---|--------|---|
| CN | 113533271 | A | 10/2021 | |
| CN | 114058721 | A | 2/2022 | |
| CN | 114324279 | A | 4/2022 | |
| CN | 115656128 | A | 1/2023 | |
| CN | 115753650 | A | 3/2023 | |
| CN | 116908154 | A | 10/2023 | |
| KR | 101777054 | B1 | 9/2017 | |
| WO | WO-9309248 | A1 * | 5/1993 | ............... C12Q 1/18 |

OTHER PUBLICATIONS

Qin Ouyang et al., "Upconversion Nanoprobes Based on a Horseradish Peroxidase-Regulated Dual-Mode Strategy for the Ultrasensitive Detection of *Staphylococcus aureus* in Meat", Journal of Agricultural and Food Chemistry, Aug. 18, 2021, vol. 69, No. 34, pp. 9947-9956.

* cited by examiner

SEQUENCE LISTING

```
Sequence total quantity: 2
SEQ ID NO: 1            moltype = DNA  length = 99
FEATURE                 Location/Qualifiers
source                  1..99
                        mol_type = other DNA
                        note = aritificial sequence
                        organism = synthetic construct
SEQUENCE: 1
tatggtcgaa taagttaacg tcccatagac tccgaactag atgatttaca gcactcccct  60
aagtaaaccg caactatgca tgttagcatt aagtcaatc                         99

SEQ ID NO: 2            moltype = DNA  length = 98
FEATURE                 Location/Qualifiers
source                  1..98
                        mol_type = other DNA
                        note = artificial sequence
                        organism = synthetic construct
SEQUENCE: 2
ataccagctt attcaattgc agggtatctg aggcttgatc tactaaatgt cgtggggcat  60
tgctattggc gttgatacgt acaatcgtaa tcagttag                          98
```

METHOD FOR DETERMINING CIPROFLOXACIN IN MEAT PRODUCT BASED ON ENZYME-LINKED UPCONVERSION FLUORESCENCE AND POTASSIUM TITANIUM OXALATE SYSTEM

CROSS-REFERENCE TO RELATED APPLICATIONS

This application is a continuation of International Patent Application No. PCT/CN2024/081570, filed on Mar. 14, 2024, which claims the benefit of priority from Chinese Patent Application No. 202310758306.2, filed on Jun. 26, 2023. The content of the aforementioned application, including any intervening amendments thereto, is incorporated herein by reference in its entirety.

REFERENCE TO AN ELECTRONIC SEQUENCE LISTING

The contents of the electronic sequence listing (SequenceListing.xml; Size: 3,225 bytes; and Date of Creation: Jun. 26, 2024) is herein incorporated by reference in its entirety.

TECHNICAL FIELD

This application relates to antibiotic detection, and more particularly to a method for determining ciprofloxacin in a meat product based on an enzyme-linked upconversion fluorescence and potassium titanium oxalate system.

BACKGROUND

Ciprofloxacin is a broad-spectrum antibacterial drug with high antibacterial activity and excellent bactericidal effect, and has been extensively used in the animal breeding and aquaculture. However, the abuse of ciprofloxacin during the breeding process will result in ciprofloxacin residues in food. Long-term intake of ciprofloxacin may reduce the human immunity and cause antibiotic resistance, eventually leading to serious functional diseases.

In view of this, the maximum residue levels of ciprofloxacin in various agricultural products and foods have been clearly specified. For example, China's national standard GB31650-2019 stipulates that the ciprofloxacin content in pork and fish must not exceed 100 μg/kg. However, traditional ciprofloxacin detection methods, such as high-performance liquid chromatography and liquid chromatography-tandem mass spectrometry, have problems such as expensive instruments and equipment, high detection cost and cumbersome steps, and cannot achieve the rapid and high-sensitivity detection of ciprofloxacin content. Therefore, it is necessary to develop a simpler and more economical ciprofloxacin detection method.

SUMMARY

An object of the present disclosure is to provide a method of determining ciprofloxacin in a meat product based on an enzyme-linked upconversion fluorescence and potassium titanium oxalate system, which can overcome the problems of high detection cost, long detection time, and cumbersome detection steps in the existing detection technologies.

In order to achieve the above object, the following technical solutions are adopted.

This application provides a method for determining ciprofloxacin in a meat product based on an enzyme-linked upconversion fluorescence and potassium titanium oxalate system, comprising:

step (1) mixing an enzyme-linked upconversion nanoparticle solution with an aptamer-bound magnetized polydopamine solution to obtain a fluorescence-ultraviolet dual-signal detection system;

step (2) establishing a fluorescence standard curve and a colorimetric standard curve for ciprofloxacin content determination through the fluorescence-ultraviolet dual-signal detection system in combination with potassium titanium oxalate and hydrogen peroxide; and step (3) determining a fluorescence intensity signal characteristic value and an ultraviolet absorbance signal characteristic value of a solution of a meat sample; and calculating a ciprofloxacin content in the meat sample according to the fluorescence standard curve and the colorimetric standard curve.

In some embodiments, the enzyme-linked upconversion nanoparticle solution is prepared through steps of:

mixing an upconversion nanoparticle, a polyacrylic acid aqueous solution, chloroform and toluene followed by stirring and centrifugal drying to obtain a carboxylated upconversion nanomaterial; and binding a complementary chain of a ciprofloxacin aptamer and horseradish peroxidase to a surface of the carboxylated upconversion nanomaterial to obtain the enzyme-linked upconversion nanoparticle solution.

In some embodiments, a ratio of the upconversion nanoparticle to the polyacrylic acid aqueous solution to chloroform to toluene is 25 mg:10 mL:2 mL:3 mL; and a ratio of the carboxylated upconversion nanomaterial to the complementary chain of the ciprofloxacin aptamer to the horseradish peroxidase is 10 mg:2.5 OD:5 mg.

In some embodiments, the aptamer-bound magnetized polydopamine solution is prepared through steps of:

ultrasonically dispersing $Fe_3O_4$ in a Tris-HCl buffer followed by addition of dopamine hydrochloride and stirring at room temperature to obtain magnetized polydopamine; and adding the magnetized polydopamine to a buffer E followed by ultrasonic dispersion, addition of the ciprofloxacin aptamer and NaCl and shaking, collecting a precipitate by means of an external magnetic field, and dissolving the precipitate in a buffer F to obtain the aptamer-bound magnetized polydopamine solution.

In some embodiments, a ratio of $Fe_3O_4$ to the Tris-HCl buffer to dopamine hydrochloride is 100 mg:200 mL:75 mg; a ratio of the magnetized polydopamine to the ciprofloxacin aptamer to NaCl is 10 mg:2.5 OD:52.65 mg; and the buffer E and the buffer F are independently a phosphate-buffered saline (PBS).

In some embodiments, a volume ratio of the enzyme-linked upconversion nanoparticle solution to the aptamer-bound magnetized polydopamine solution is 1-1.5:0.5.

In some embodiments, the step (2) is performed through steps of:

adding each of a series of ciprofloxacin standard solutions varying in concentration into the fluorescence-ultraviolet dual-signal detection system followed by magnetic separation to obtain a supernatant;

detecting a fluorescence intensity signal characteristic value of the supernatant;

adding a hydrogen peroxide aqueous solution to the supernatant for reaction for a period of time followed by addition of a potassium titanium oxalate solution to obtain a light-yellow solution;

detecting an ultraviolet absorbance of the light-yellow solution; and plotting the fluorescence standard curve and the colorimetric standard curve based on fluorescence intensity signal characteristic values and ultraviolet absorbance signal characteristic values of the series of ciprofloxacin standard solutions.

In some embodiments, the method further comprises:

preparing the solution of the meat sample; determining the fluorescence intensity signal characteristic value and the ultraviolet absorbance signal characteristic value of the solution of the meat sample; and calculating the ciprofloxacin content in the meat sample according to the fluorescence standard curve and the colorimetric standard curve.

In some embodiments, in step (3), the solution of the meat sample is prepared through steps of:

beating the meat sample into a homogenate, adding acidified acetonitrile and anhydrous sodium sulfate to the homogenate followed by shaking and centrifugation to obtain a precipitate and a first supernatant, adding acidified acetonitrile to the precipitate followed by shaking and centrifugation to obtain a second supernatant; and combining the first supernatant with the second supernatant followed by addition of n-hexane and shaking, and collecting a bottom-layer phase, and subjecting the bottom-layer phase to rotary evaporation, addition of methanol and filtration to obtain the solution of the meat sample.

Compared to the prior art, the present disclosure has the following beneficial effects.

(1) This application adopts the magnetized polydopamine as an energy receptor and signal separator. Magnetized polydopamine is also an effective quencher, which can effectively quench the fluorescence of up-conversion fluorescent materials through the fluorescence resonance energy transfer, such that the fluorescence of enzyme-linked upconversion materials can be rapidly quenched, thereby improving the detection efficiency. Compared to traditional quenchers, such as gold nanoparticles, manganese dioxide, and graphene oxide, the magnetized polydopamine has a signal separation effect as well as excellent magnetic properties, such that it can be effectively separated from the interferent without the need for time-consuming centrifugal filtration. The use of magnetized polydopamine to separate a target from coexisting ions can eliminate the interference of actual samples and improve the detection sensitivity, efficiency and reliability, so as to achieve the trace detection of the target.

(2) The potassium titanium oxalate solution used in this application can sensitively and selectively react with $H_2O_2$ to generate yellow peroxotitanic acid, so as to produce a colorimetric signal. In the presence of ciprofloxacin, the ciprofloxacin will bind to the aptamer on the surface of the magnetized polydopamine, such that the magnetized polydopamine is separated from the enzyme-linked upconversion nanoparticle. The magnetized polydopamine precipitate is removed by magnetic separation. The enzyme-linked upconversion nanoparticle is retained in the supernatant, and the concentration of the enzyme-linked upconversion nanoparticle in the supernatant is positively correlated with the ciprofloxacin content in the sample. After introducing $H_2O_2$ to the supernatant, the horseradish peroxidase bound to the enzyme-linked upconversion nanoparticle will catalyze the decomposition of $H_2O_2$, thereby reducing the $H_2O_2$ level. The reaction of potassium titanium oxalate with $H_2O_2$ in an acidic environment is expressed as: $TiO_2+H_2O_2 \rightarrow [TiO(H_2O_2)]^{2+}$, where the color intensity of the resultant yellow complex $[TiO(H_2O_2)]^{2+}$ varies with the $H_2O_2$ concentration, such that a content of ciprofloxacin in a tested sample can be accurately calculated by detecting the absorbance value of the solution. The absorbance is positively correlated with the $H_2O_2$ level, and the ciprofloxacin content is negatively correlated with the $H_2O_2$ level, so that the higher the absorbance, the lower the ciprofloxacin content. The reaction between potassium titanium oxalate and $H_2O_2$ is rapid, mild and readily operable, thereby shortening the detection time and improving the detection efficiency.

(3) The enzyme-linked up-conversion fluorescent material prepared in the present disclosure combined with the magnetized polydopamine can achieve fluorescence-colorimetric dual signal response to ciprofloxacin. The detection sensitivity and reliability can be improved by precisely controlling a ratio of the enzyme-linked upconversion fluorescent material to the magnetized polydopamine. Compared to existing detection methods based on upconversion materials, the system constructed in the present disclosure can generate two detection signals, leading to more accurate detection results.

BRIEF DESCRIPTION OF THE DRAWINGS

The accompanying drawings constituting a part of this application are intended to provide a further understanding of the present disclosure. The embodiments of the present disclosure and descriptions thereof are intended to explain the present disclosure, and are not intended to limit the scope of the present disclosure.

DETAILED DESCRIPTION OF EMBODIMENTS

The embodiments of the present disclosure will be described in detail below. The detailed description of the embodiments should not be construed as limitations of the present disclosure, but rather as a more detailed description of certain aspects, features and technical solutions of the disclosure.

It should be understood that terms used herein are only intended to describe the embodiments, and are not intended to limit the present disclosure. In addition, for numerical ranges in the present disclosure, it should be understood that each intervening value between upper and lower limits of a range is also specifically disclosed. Each smaller range between any stated value or intervening value within a stated range and any other stated value or intervening value within a stated range is also included within the disclosure. The upper and lower limits of these smaller ranges can independently be included or excluded from the range.

Unless defined otherwise, all technical and scientific terms used herein have the same meaning as commonly understood by those of ordinary skill in the art. Although only illustrative methods and materials are described herein, any methods and materials similar or equivalent to these described herein can be used in the practice or testing of the disclosure. All literatures mentioned herein are incorporated by reference to disclose and describe the related methods and/or materials. In the event of conflict with any incorporated literature, the contents of this specification shall prevail.

It is obvious to those skilled in the art that various modifications and changes can be made to the embodiments described herein without departing from the scope or spirit of the present disclosure. Other embodiments obtained in accordance with the specification of the present disclosure are obvious to those skilled in the art. The specification and embodiments merely illustrative.

As used herein, "comprise", "include", "have", "contain", etc. are all open terms, which mean "including but not limited to".

The term "room temperature" mentioned in the present disclosure is defined as 25±2° C. unless otherwise specified.

Raw materials used in the following examples of the present disclosure are all commercially available.

This application provides a method for determining ciprofloxacin in a meat product based on an enzyme-linked upconversion fluorescence and potassium titanium oxalate system, which includes the following steps.

Step (1) Preparation of Carboxylated Upconversion Nanomaterial

Yttrium chloride hexahydrate ($YCl_3 \cdot 6H_2O$), ytterbium chloride hexahydrate ($YbCl_3 \cdot 6H_2O$) and erbium chloride hexahydrate ($ErCl_3 \cdot 6H_2O$) are dispersed in anhydrous methanol A. Oleic acid and 1-octadecene are added to the anhydrous methanol A to obtain a mixture. Under a nitrogen atmosphere, the mixture is subjected to first stirring under heating followed by cooling to room temperature. The mixture is removed from the nitrogen atmosphere, dropwise added with a mixed solution of sodium hydroxide (NaOH) and ammonium fluoride ($NH_4F$) dissolved in anhydrous methanol B, and subjected to second stirring under heating. Under a nitrogen atmosphere, the mixture is subjected to third stirring under heating for reaction, cooled to room temperature, and centrifuged to obtain an upconversion nanoparticle precipitate. The upconversion nanoparticle precipitate is washed with a mixed solution of cyclohexane and ethanol, and dried to obtain a pure upconversion nanoparticle.

The upconversion nanoparticle, a polyacrylic acid aqueous solution, chloroform and toluene are mixed in proportion, subjected to fourth stirring for reaction and centrifugal drying to obtain the carboxylated upconversion nanomaterial.

Step (2) Bonding of Complementary Chain of Ciprofloxacin Aptamer and Horseradish Peroxidase to Surface of Carboxylated Upconversion Nanomaterial The carboxylated upconversion nanomaterial is dissolved in a buffer A followed by addition of a 1-ethyl-(3-dimethylaminopropyl) carbodiimide hydrochloride aqueous solution and an N-hydroxysulfosuccinimide aqueous solution, a first mixing under shaking at a preset temperature and centrifugal cleaning with deionized water A. The resulting precipitate is dispersed in a buffer B followed by addition of a solution of the complementary chain of the ciprofloxacin aptamer and horseradish peroxidase, second mixing under shaking at a preset temperature, centrifugal cleaning with deionized water B, and dissolving in a buffer C to obtain an enzyme-linked upconversion nanoparticle solution. An enzyme-linked upconversion fluorescent material acts as energy donor and colorimetric signal source to simultaneously provide both fluorescent and colorimetric signals, facilitating more accurate detection of ciprofloxacin.

Step (3) $FeCl_3 \cdot 6H_2O$ and $FeSO_4 \cdot 7H_2O$ are dissolved in deionized water C, introduced with nitrogen, stirred, added with $NH_3 \cdot H_2O$, and subjected to first stirring under heating for reaction. After the reaction is completed, the obtained $Fe_3O_4$ is separated from the reaction solution using a strong magnet, rinsed with ultrapure water at least three times to effectively remove excess $NH_3 \cdot H_2O$, and dried in a vacuum oven to obtain dry $Fe_3O_4$. A preset amount of $Fe_3O_4$ is dispersed ultrasonically in a buffer D followed by addition of dopamine hydrochloride and second stirring at room temperature to obtain magnetized polydopamine. The magnetized polydopamine is collected by magnet adsorption, washed three times with deionized water and ethanol and dried.

Step (4) Bonding of Magnetized Polydopamine to Aptamer

Dry magnetized polydopamine is dispersed ultrasonically in a buffer E followed by addition of the ciprofloxacin aptamer and NaCl, shaking for a period of time, and washing with deionized water. A precipitate is collected by means of an external magnetic field. The precipitate is dissolved in a buffer F to obtain an aptamer-bound magnetized polydopamine solution. The aptamer-bound magnetized polydopamine can specifically recognize ciprofloxacin. Therefore, the method provided herein has excellent selectivity and interference resistance.

Step (5) Preparation of Potassium Titanium Oxalate Solution

Potassium titanium oxalate, sulfamic acid and deionized water C are mixed in proportion to prepare the potassium titanium oxalate solution. The potassium titanium oxalate solution can selectively react with hydrogen peroxide to generate yellow peroxotitanic acid, such that an absorbance value of the solution can be changed with accordance to a change in an amount of hydrogen peroxide, thereby achieving colorimetric detection.

Step (6) Preparation of Fluorescence-Ultraviolet Dual-Signal Detection System

The enzyme-linked upconversion nanoparticle solution obtained in step (2) is subjected to mixing with the aptamer-bound magnetized polydopamine solution prepared in step (4) in proportion for a period of time, so as to obtain the fluorescence-ultraviolet dual-signal detection system.

Step (7) Establishment of Fluorescence Standard Curve and Colorimetric Standard Curve for Ciprofloxacin Content Determination Each of a series of ciprofloxacin standard solutions varying in concentrations is prepared followed by addition of the detection system obtained in step (5) and magnetic separation to obtain a supernatant. A fluorescence intensity signal characteristic value of the supernatant is detected. The supernatant is added with a hydrogen peroxide aqueous solution for reaction for a period of time followed by addition of the potassium titanium oxalate solution to obtain a light-yellow solution. An ultraviolet absorbance of the light-yellow solution is detected. The fluorescence standard curve and the colorimetric standard curve related to ciprofloxacin concentration are plotted based on fluorescence intensity signal characteristic values and ultraviolet absorbance characteristic values of the series of ciprofloxacin standard solutions.

Step (8) Determination of Ciprofloxacin Content in Meat Sample

The meat sample is beat into a homogenate, added with acidified acetonitrile A and anhydrous sodium sulfate, shaken for 15 min and centrifuged to obtain a first supernatant and a precipitate. The precipitate is added with acidified acetonitrile B, shaken, and centrifuged to obtain a second supernatant. The first supernatant is combined with the second supernatant, placed in a separatory funnel, added with n-hexane, and shaken. A bottom-layer phase is collected and subjected to rotary evaporation to dryness, addition of a methanol C solution and filtration through a filter membrane to obtain a solution of the meat sample. A fluorescence intensity signal characteristic value and an ultraviolet absorbance signal characteristic value of the solution of the meat sample are determined. A ciprofloxacin content in the meat sample is calculated according to the fluorescence standard curve and the colorimetric standard curve obtained in step (7).

In some embodiments, in step (1), a mass ratio of yttrium chloride hexahydrate to ytterbium chloride hexahydrate to erbium chloride hexahydrate is 236.6:77.5:7.6, a ratio of methanol A to oleic acid to 1-octadecene to $NH_4F$ to NaOH to methanol B is 6-10 mL:6 mL:15 mL:0.1482 g:0.1 g:10 mL, the first stirring under heating is performed at 160° C.-170° C. for 20-30 min, the second stirring under heating is performed at 60° C.-70° C. for 60-70 min, and the third stirring under heating is performed at 290° C.-300° C. for 60-90 min.

A ratio of the upconversion nanoparticle to the polyacrylic acid aqueous solution to chloroform to toluene is 25 mg:10 mL:2 mL:3 mL. A concentration of the polyacrylic acid aqueous solution is 15 mg/mL. The fourth stirring is performed for 40-60 h.

In some embodiments, in step (2), a ratio of the carboxylated upconversion nanomaterial to the buffer A to the 1-ethyl-(3-dimethylaminopropyl) carbodiimide hydrochloride aqueous solution to the N-hydroxysulfosuccinimide aqueous solution is 10 mg:10 mL:0.5 mL:0.5 mL, a concentration of the 1-ethyl-(3-dimethylaminopropyl) carbodiimide hydrochloride aqueous solution is 2.0 mg/mL, a concentration of the N-hydroxysulfosuccinimide aqueous solution is 1.0 mg/mL, a ratio of the carboxylated upconversion nanomaterial to the solution of the complementary chain of the ciprofloxacin aptamer to the horseradish peroxidase is 10 mg:2.5 OD:5 mg, a volume of the buffer B is 10 mL, a volume of the buffer C is 40 mL, the buffer A is a Tris-HCl buffer with a pH value of 8.5, the buffer B is a Tris-HCl buffer with a pH value of 8.5, and the buffer C is a phosphate buffer with a pH value of 5.

In some embodiments, in step (3), a ratio pf $FeCl_3 \cdot 6H_2O$ to $FeSO_4 \cdot 7H_2O$ to $NH_3 \cdot H_2O$ is 3.8-4.2 g:2.3-2.4 g:25 mL, a ratio of $Fe_3O_4$ to the buffer D to dopamine hydrochloride is 100 mg:200 mL:75 mg, the first stirring under heating is performed at 80° C. for 60 min, the second stirring under heating is performed for 6-10 h, the buffer D is a Tris-HCl buffer with a pH value of 8.5.

In some embodiments, in step (4), a ratio of the buffer E to the magnetized polydopamine to the ciprofloxacin aptamer to NaCl is 6 mL:10 mg:2.5 OD:52.65 mg, the shaking is performed at 37° C. for 24-30 h, the buffer E is a phosphate-buffered saline (PBS) with a pH value of 6.8, and the buffer F is a PBS with a pH value of 6.8 and a volume of 20 mL.

In some embodiments, in step (5), a ratio of potassium titanium oxalate to sulfamic acid to deionized water C is 4 mg:2 mg:1 mL.

In some embodiments, in step (6), a volume ratio of the enzyme-linked upconversion nanoparticle solution to the aptamer-bound magnetized polydopamine solution is 1-1.5:0.5, and the mixing is performed for 20-30 min.

In some embodiments, in step (7), a concentration of the hydrogen peroxide aqueous solution is 8 mmol/L, and a volume ratio of the ciprofloxacin standard solution to the hydrogen peroxide aqueous solution is 2:1.

In some embodiments, in step (8), a ratio of the meat sample to the acidified acetonitrile A to the anhydrous sodium sulfate is 5 g:30 mL:30 g, a ratio of the meat sample to the acidified acetonitrile B to n-hexane to the anhydrous methanol Cis 5 g:30 mL:25 mL:1 mL.

The magnetized polydopamine used in this application not only has excellent magnetism of magnetic nanoparticles, which can separate a target from coexisting ions and eliminate the interference of other substances, but also has excellent quenching performance of polydopamine, such that the fluorescence of enzyme-linked up-conversion fluorescent materials can be quenched. It is proved by detecting a hysteresis loop of the magnetized polydopamine that the magnetized polydopamine has excellent magnetism properties, such that the target can be rapidly separated from the interferent by using an external magnetic field. Changes in fluorescence lifetime before and after the enzyme-linked up-conversion fluorescent material and the magnetized polydopamine are mixed are detected, and the fluorescence lifetime decreases after mixing, which verifies that the magnetized polydopamine can effectively quench the fluorescence of the enzyme-linked upconversion fluorescent material. In addition, there are different types of functional groups in the polydopamine, such as o-quinone, amino, imine groups and carboxyl groups. For one thing, these functional groups can chelate with metal ions, ensuring the adhesion of a polydopamine layer to a surface of metal or metal oxides. For another, the carboxyl groups on the surface of the polydopamine can covalently bind to an aminated aptamer, which improves the stability of the aptamer-bound magnetized polydopamine.

The potassium titanium oxalate solution can selectively react with hydrogen peroxide to generate yellow peroxotitanic acid, thereby achieving colorimetric detection. The principle is that in an acidic environment: $TiO^{2+}+H_2O_2 \rightarrow [TiO(H_2O_2)]^{2+}$, where $[TiO(H_2O_2)]^{2+}$ is a stable yellow complex with a color intensity positively correlated with the $H_2O_2$ concentration. Therefore, a concentration of ciprofloxacin contained in the sample can be determined by detecting the absorbance of peroxotitanic acid. The present disclosure proposes an efficient dual-mode fluorescence and colorimetric method for determining ciprofloxacin adopting a fluorescence quenching performance and magnetic separation effect of the magnetized polydopamine and a chromogenic effect of the potassium titanium oxalate solution, which can be used for actual sample detection.

The methanol and deionized water with different letters mentioned above are only intended to distinguish different samples, and do not represent different compositions. For example, methanol A and methanol B only represent two methanol reagents used separately, which have the same composition.

In order to further verify the detection effect of the method of the disclosure on organic ciprofloxacin in a meat product, the present disclosure provides the following embodiments regarding a determination of ciprofloxacin in fish meat.

Example 1

Step (1) Preparation of Carboxylated Upconversion Nanomaterial 236.6 mg of $YCl_3 \cdot 6H_2O$, 77.5 mg of $YbCl_3 \cdot 6H_2O$ and 7.6 mg of $ErCl_3 \cdot 6H_2O$ were dissolved in 10 mL of methanol, and subjected to ultrasonic dispersion followed by pouring into a three-neck flask. The three-necked flask was added with 6 mL of oleic acid and 15 mL of 1-octadecene to obtain a mixed solution and introduced with nitrogen. The mixed solution was stirred at 160° C. for 30 min and cooled to room temperature. 10 mL of methanol solution containing 0.1482 g of $NH_4F$ and 0.1 g of NaOH was dropwise added into the three-neck flask under stirring, heated to 70° C. and kept for 70 min to remove methanol. After the methanol was removed, the three-neck flask was introduced with nitrogen, and the mixed solution was gradually heated to 300° C. and maintained for 80 min under constant stirring. After the reaction was completed, the reaction solution was stopped heating and naturally cooled to room temperature. An oleic acid-coated upconversion nanomaterial was collected by centrifugation, washed several times with cyclohexane and ethanol, and dried in an oven at 60° C. 6 mL of toluene and 4 mL of chloroform were added to 50 mg of the oleic acid-coated upconversion nanomaterial, and then 20 mL of 15 mg/mL polyacrylic acid aqueous solution was added and stirred for 48 h. Finally, the carboxylated upconversion nanomaterial solution was separated by centrifugation, washed three times with ultrapure water to remove excess polyacrylic acid, and dried to obtain the carboxylated upconversion nanomaterial (as shown in FIG. 1).

Figure 1:
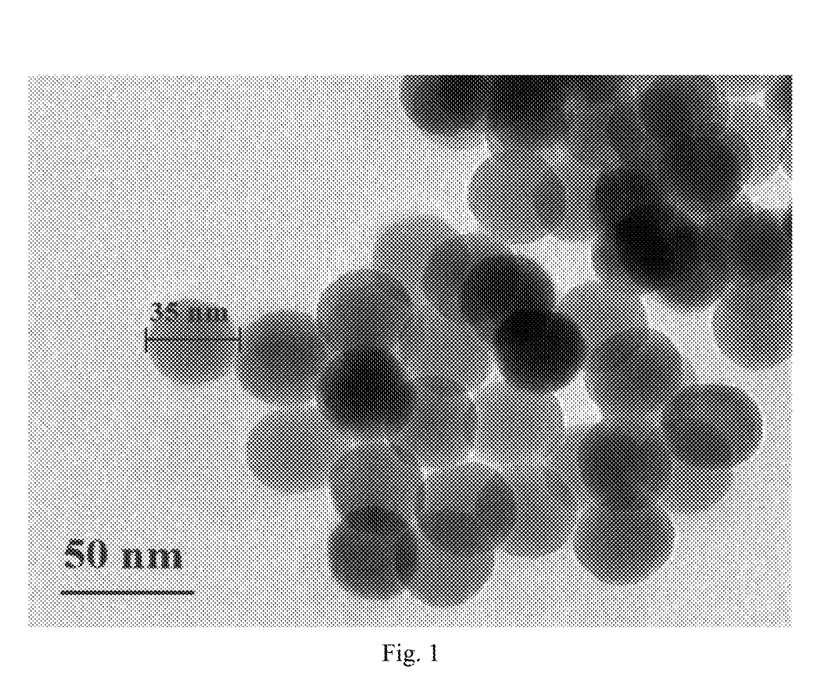
FIG. 1 is a transmission electron microscopy (TEM) image of an upconversion fluorescent nanomaterial in accordance with an embodiment of the present disclosure.

It can be seen form FIG. 1 that carboxyl groups on a surface of the carboxylated nanomaterial can be connected to an aminated aptamer complementary chain by covalent binding, leading to a stronger connection. Compared with the oleic acid-coated upconversion nanomaterial, the carboxylated nanomaterial has better water solubility and dispersion, which facilitates actual sample detection.

Step (2) Bonding of Complementary Chain of Ciprofloxacin Aptamer and Horseradish Peroxidase to Surface of Carboxylated Upconversion Nanomaterial 10 mL of a Tris-HCl buffer, 0.5 mL of a 1.0 mg/mL N-hydroxysulfosuccinimide aqueous solution and 0.5 mL of a 2.0 mg/mL 1-ethyl-(3-dimethylaminopropyl) carbodiimide hydrochloride aqueous solution were added to 10 mg of the carboxylated upconversion nanomaterial followed by stirring at 4° C. for 2 h and centrifugal cleaning with deionized water. A first precipitate was collected, dispersed in 10.0 mL of a Tris-HCl buffer, added with 2.5 OD of a ciprofloxacin aptamer complementary chain (TATGGT-CGAATAAGTTAACGTCCCATAGACTCCGAACTA-GATGATTTACAG CACTCCCCTAAGTAAACCGCAAC-TATGCATGTTAGCATTAAGTCAATC-$(CH_2)_6$—$NH_2$-5', SEQ ID NO: 1) and 5 mg of horseradish peroxidase, stirred slowly at 4° C. for 12 h, and centrifuged to obtain a second precipitate. The second precipitate was washed with ultrapure water to obtain the enzyme-linked upconversion fluorescent material (recorded as cDNA-UCNPs-HRP). Finally, the enzyme-linked upconversion fluorescent material was resuspended in 40 mL of a phosphate buffer with a pH value of 5 and stored at 4° C. for subsequent use.

Step (3) Preparation of Magnetized Polydopamine 4.1 g of $FeCl_3 \cdot 6H_2O$ and 2.35 g of $FeSO_4 \cdot 7H_2O$ were dissolved in 100 mL of ultrapure water and stirred magnetically under a nitrogen atmosphere for 20 min. 25 mL of $NH_3 \cdot H_2O$ was added to the mixture and stirred at 80° C. for 60 min for reaction. After the reaction was completed, the obtained $Fe_3O_4$ was separated from the reaction solution by a strong magnet, and washed with ultrapure water at least three times to remove excess $NH_3 \cdot H_2O$. Finally, the resulting product was dried in a vacuum oven at 50° C. to obtain dry $Fe_3O_4$.

Figure 2:
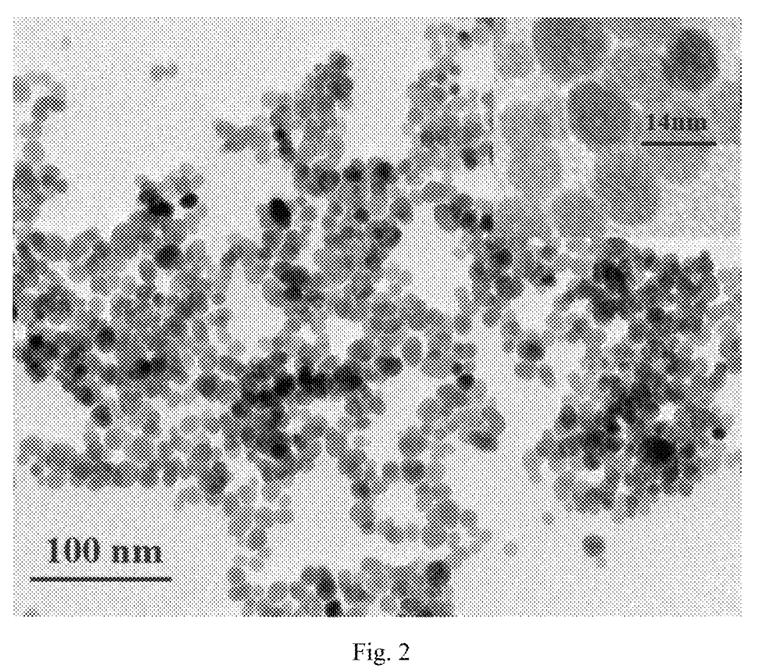
FIG. 2 is a TEM image of magnetized polydopamine in accordance with an embodiment of the present disclosure.

100 mg of $Fe_3O_4$ was dispersed ultrasonically in 200 mL of a Tris-HCl buffer followed by addition of 75 mg of dopamine hydrochloride and stirring at room temperature for 8 h. The magnetized polydopamine was collected by magnet adsorption, washed three times with deionized water and ethanol, and dried in an oven at 60° C. for 12 h (as shown in FIGS. 2-3).

Figure 3:
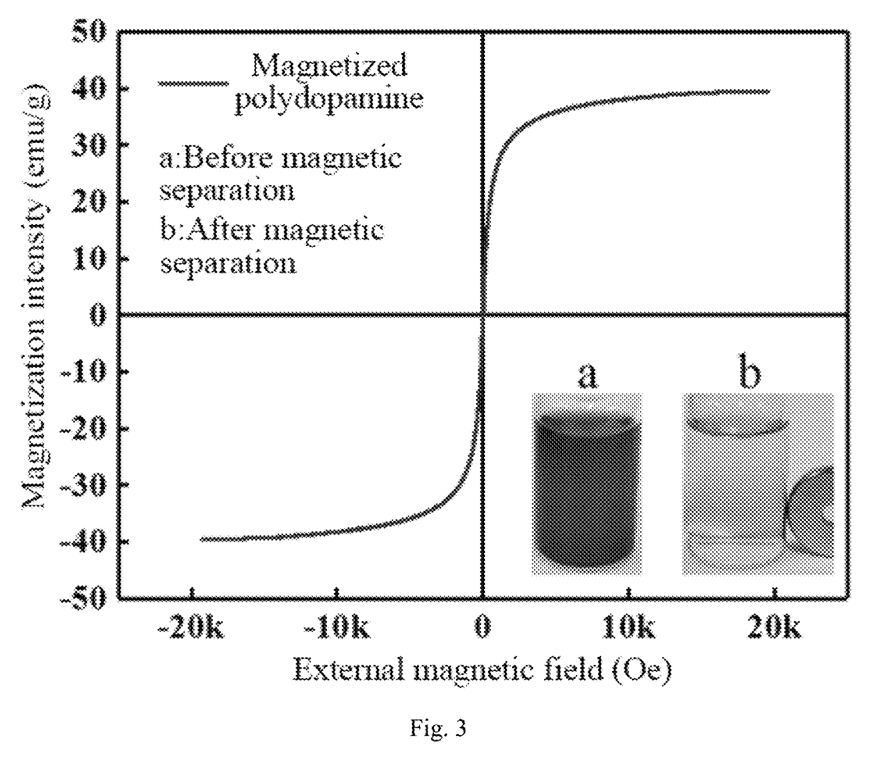
FIG. 3 shows a magnetic hysteresis loop of the magnetized polydopamine in accordance with an embodiment of the present disclosure.

It can be seen form FIG. 3 that the magnetized polydopamine had excellent quenching properties and can effectively quench the fluorescence of enzyme-linked upconversion fluorescent materials to regulate the fluorescence signal. The magnetized polydopamine also had excellent magnetic properties, which facilitated signal separation, such that it can be effectively separated from interferents without the need for time-consuming centrifugal filtration. The use of the magnetized polydopamine to separate a target from coexisting ions can eliminate interference from the actual sample and achieve trace detection of the target.

Step (4) Bonding of Magnetized Polydopamine to Aptamer 10 mg of magnetized polydopamine was added into 6 mL of a PBS (pH value of 6.8) and dispersed ultrasonically. 2.5 OD of a ciprofloxacin aptamer (5'-$NH_2$—$(CH_2)_6$ ATA CCA GCT TAT TCA ATT GCA GGG TAT CTG AGG CTT GAT CTA CTA AAT GTC GTG GGG CAT TGC TAT TGG CGT TGA TAC GTA CAA TCG TAA TCA GTT AG-3', SEQ ID NO: 2) and 52.65 mg of NaCl were added to the mixture, shaken at 37° C. for 24 h and washed several times with deionized water to remove unbonded ciprofloxacin aptamer. The resulting precipitate was redispersed in 20 mL of a PBS (pH value of 6.8) to obtain an aptamer-bound magnetized polydopamine solution, which was stored at 4° C.

Step (5) Preparation of Potassium Titanium Oxalate Solution 100 mg of sulfamic acid and 200 mg of potassium titanium oxalate were dissolved in 50 mL of deionized water followed by shaking to prepare the potassium titanium oxalate solution with a concentration of 2 mg/mL.

Step (6) Preparation of Fluorescence-Ultraviolet Dual-Signal Detection System

200 μL of the enzyme-linked upconversion fluorescent material was mixed with 100 μL of the aptamer-bound magnetized polydopamine followed by incubating at 37° C. for 20 min to obtain the fluorescence-ultraviolet dual-signal detection system.

Figure 4A:
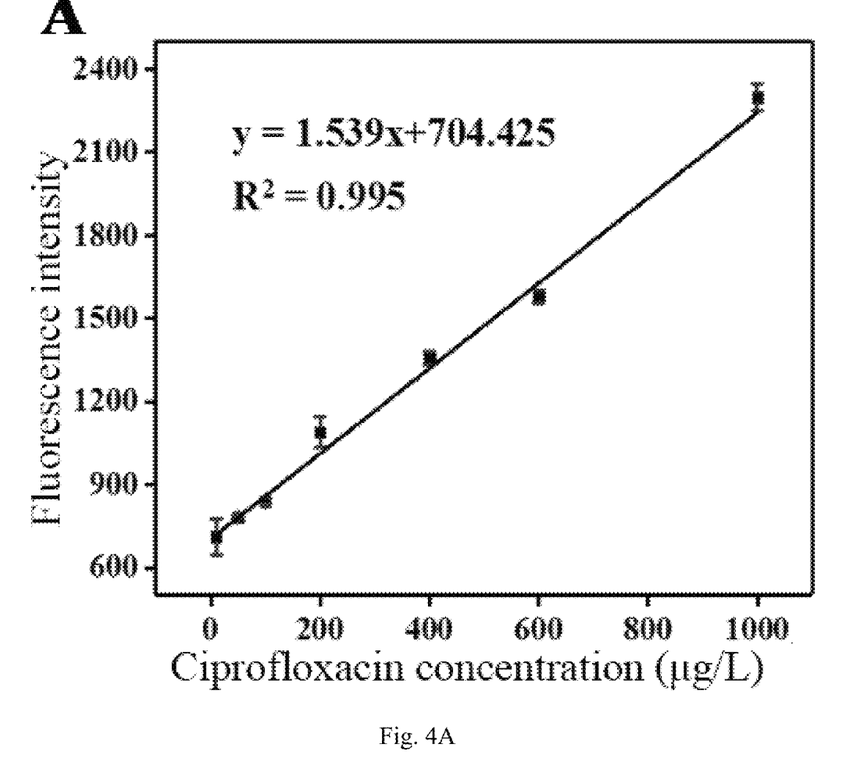
FIG. 4A shows a standard curve of fluorescence intensity versus ciprofloxacin concentration.
Figure 4B:
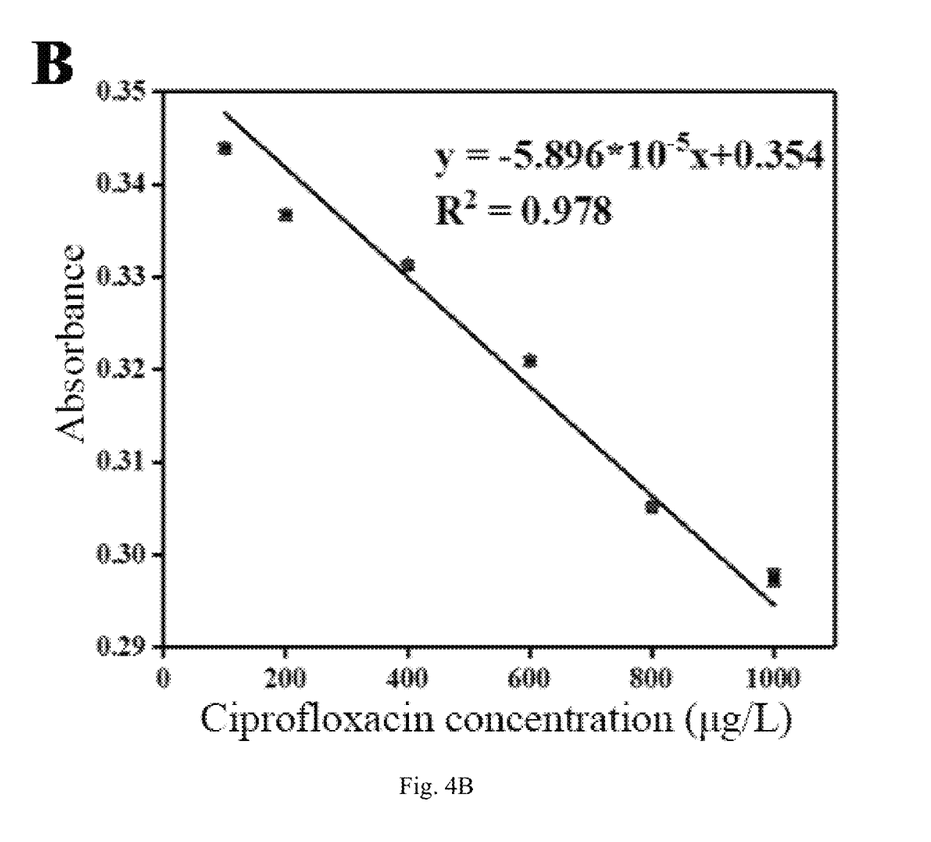
FIG. 4B shows a standard curve of ultraviolet absorbance versus ciprofloxacin concentration.

Step (7) Establishment of Fluorescence Standard Curve and Colorimetric Standard Curve for Ciprofloxacin Content Detection Each of a series of 200 μL of ciprofloxacin solutions varying in concentrations (10, 50, 100, 200, 400, 600, 800 and 1000 μg/L) was prepared followed by mixing with the fluorescence-ultraviolet dual-signal detection system and magnetic separation to obtain a supernatant. A fluorescence intensity signal characteristic value of the supernatant was detected. The supernatant was added with 100 μL of 8 mmol/L hydrogen peroxide aqueous solution for reaction for 1 h, and then added with the potassium titanium oxalate solution to obtain a light-yellow solution. An ultraviolet absorbance of the light-yellow solution is detected. An ultraviolet standard curve and a fluorescence standard curve (as shown in FIG. 4) related to ciprofloxacin concentration were plotted based on fluorescence intensity signal characteristic values and ultraviolet absorbance characteristic values of the series of ciprofloxacin standard solutions.

Step (8) Determination of Ciprofloxacin Content in Fish Sample 5 g of the fish sample was beat into a homogenate, added with 30 mL of acidified acetonitrile and 30 g of anhydrous sodium sulfate, shaken for 15 min, and centrifuged to obtain a precipitate and a first supernatant. The precipitate was added with 30 mL of acidified acetonitrile, shaken, and centrifuged to obtain a second supernatant. The first supernatant and the second supernatant were added into a separatory funnel. 25 mL of n-hexane was added into the separatory funnel and shaken. A bottom-layer phase is collected and subjected to rotary evaporation to dryness, addition of 1 mL of a methanol solution and filtration through a filter membrane to obtain a solution of the fish sample. A fluorescence intensity signal characteristic value and an ultraviolet absorbance signal characteristic value of the solution of the fish sample were determined. A ciprofloxacin content in the fish sample was calculated according to the fluorescence standard curve and the colorimetric standard curve obtained in step (7).

A ciprofloxacin content of each of three fish samples was determined using the determination method and steps described in Example 1, and verified using the national standard method (GB-31656.3-2021). The determination results were shown in Table 1.

TABLE 1

Determination results of ciprofloxacin in fish samples respectively using determination method of the present disclosure and high-performance liquid chromatography (HPLC)

| | HPLC | | Determination method of the present disclosure | | | | | |
|---|---|---|---|---|---|---|---|---|
| | | | Fluorescence result | | | Ultraviolet result | | |
| Sample | Detection concentration (μg/kg) | Coefficient of variation (%) | Detection concentration (μg/kg) | Coefficient of variation (%) | t-test | Detection concentration (μg/kg) | Coefficient of variation (%) | t-test |
| Fish | 675.30 ± 23.55 | 3.49 | 685.80 ± 21.01 | 3.07 | P > 0.05 | 701.04 ± 11.29 | 1.61 | P > 0.05 |
| | 359.80 ± 24.44 | 6.79 | 358.03 ± 6.42 | 1.79 | | 342.61 ± 3.39 | 0.99 | |
| | 58.18 ± 5.80 | 9.97 | 63.29 ± 8.21 | 12.97 | | 66.15 ± 5.88 | 8.88 | |

The value of P of the t-test represents the probability of a sample observation result or a more extreme result occurring when the null hypothesis is true, and P > 0.05 indicates that there is no significant difference in the results.

It can be seen form Table 1 that there is no significant difference between the detection results of the determination method of the present disclosure and those of HPLC, which indicates that the determination method of the present disclosure has excellent accuracy in actual samples and promising application prospects.

Comparative Example 1

The steps of Comparative Example 1 were the same as Example 1, except that step (6) was that: 100 μL of the enzyme-linked upconversion fluorescent material was mixed with 100 μL of magnetized polydopamine followed by incubating at 37° C. for 20 min to obtain a fluorescence-ultraviolet dual-signal detection system.

The determination method in Comparative Example 1 was performed to determine the ciprofloxacin content in fish meat, and the results demonstrated that the determination method in Comparative Example 1 had a lower detection accuracy compared to the method provided in Example 1.

Comparative Example 2

The steps of Comparative Example 2 were the same as Example 1, except that step (2) was absent, and step (6) was that: 200 μL of the carboxylated upconversion nanomaterial prepared in step (1) was mixed with 100 μL of magnetized polydopamine followed by incubating at 37° C. for 20 min to obtain a fluorescence-ultraviolet dual-signal detection system.

The determination method in Comparative Example 2 was performed to determine the ciprofloxacin content in fish meat, and the results demonstrated that the determination method in Comparative Example 2 had a lower detection accuracy compared to the method provided in Example 1.

The embodiments described above are merely illustrative of the present disclosure, and are not intended to limit the scope of the present disclosure. It should be understood that various changes or substitutions made by those of ordinary skill in the art without departing from the spirit of the present disclosure shall fall within the scope of the present disclosure defined by the appended claims.

What is claimed is:

1. A method for determining ciprofloxacin in a meat product based on an enzyme-linked upconversion fluorescence and potassium titanium oxalate system, comprising:
    step (1) mixing an enzyme-linked upconversion nanoparticle solution with an aptamer-bound magnetized polydopamine solution to obtain a fluorescence-ultraviolet dual-signal detection system;
    step (2) establishing a fluorescence standard curve and a colorimetric standard curve for ciprofloxacin content determination through the fluorescence-ultraviolet dual-signal detection system in combination with potassium titanium oxalate and hydrogen peroxide; and
    step (3) subjecting a meat sample to homogenization, dissolution by an organic solvent, centrifugation and filtration to obtain a solution of the meat sample; determining a fluorescence intensity signal characteristic value and an ultraviolet absorbance signal characteristic value of the solution of the meat sample; and calculating a ciprofloxacin content in the meat sample according to the fluorescence standard curve and the colorimetric standard curve;
    wherein the enzyme-linked upconversion nanoparticle solution is prepared through steps of:
    mixing an upconversion nanoparticle, a polyacrylic acid aqueous solution, chloroform and toluene followed by stirring and centrifugal drying to obtain a carboxylated upconversion nanomaterial; and
    binding a complementary chain of a ciprofloxacin aptamer and horseradish peroxidase to a surface of the carboxylated upconversion nanomaterial to obtain the enzyme-linked upconversion nanoparticle solution;
    the aptamer-bound magnetized polydopamine solution is prepared through steps of:
    ultrasonically dispersing $Fe_3O_4$ in a Tris-HCl buffer followed by addition of dopamine hydrochloride and stirring at room temperature to obtain magnetized polydopamine; and
    adding the magnetized polydopamine to a buffer E followed by ultrasonic dispersion, addition of the ciprofloxacin aptamer and NaCl and shaking, collecting a precipitate by means of an external magnetic field, and dissolving the precipitate in a buffer F to obtain the aptamer-bound magnetized polydopamine solution;
    wherein the buffer E and the buffer F are independently a phosphate-buffered saline (PBS).

2. The method of claim 1, wherein a ratio of the upconversion nanoparticle to the polyacrylic acid aqueous solution to chloroform to toluene is 25 mg: 10 mL: 2 mL: 3 mL; and a ratio of the carboxylated upconversion nanomaterial to the complementary chain of the ciprofloxacin aptamer to the horseradish peroxidase is 10 mg: 2.5 OD: 5 mg.

3. The method of claim 1, wherein a ratio of $Fe_3O_4$ to the Tris-HCl buffer to dopamine hydrochloride is 100 mg: 200 mL: 75 mg; and a ratio of the magnetized polydopamine to the ciprofloxacin aptamer to NaCl is 10 mg: 2.5 OD: 52.65 mg.

4. The method of claim 1, wherein a volume ratio of the enzyme-linked upconversion nanoparticle solution to the aptamer-bound magnetized polydopamine solution is 1-1.5: 0.5; and in step (1), the enzyme-linked upconversion nanoparticle solution and the aptamer-bound magnetized polydopamine solution are mixed for 20-30 min.

5. The method of claim 1, wherein the step (2) is performed through steps of:
    adding each of a series of ciprofloxacin standard solutions varying in concentration into the fluorescence-ultraviolet dual-signal detection system followed by magnetic separation to obtain a supernatant;
    detecting a fluorescence intensity signal characteristic value of the supernatant;
    adding a hydrogen peroxide aqueous solution to the supernatant for reaction for a period of time followed by addition of a potassium titanium oxalate solution to obtain a light-yellow solution;
    detecting an ultraviolet absorbance of the light-yellow solution; and
    plotting the fluorescence standard curve and the colorimetric standard curve based on fluorescence intensity signal characteristic values and ultraviolet absorbance signal characteristic values of the series of ciprofloxacin standard solutions.

6. The method of claim 1, wherein in step (3), the solution of the meat sample is prepared through steps of:
    beating the meat sample into a homogenate, adding acidified acetonitrile and anhydrous sodium sulfate to the homogenate followed by shaking and centrifugation to obtain a precipitate and a first supernatant, adding acidified acetonitrile to the precipitate followed by shaking and centrifugation to obtain a second supernatant; and combining the first supernatant with the second supernatant followed by addition of n-hexane and shaking, and collecting a bottom-layer phase, and subjecting the bottom-layer phase to rotary evaporation, addition of methanol and filtration to obtain the solution of the meat sample.

* * * * *